United States Patent
Maruyama

(10) Patent No.: US 9,661,985 B2
(45) Date of Patent: *May 30, 2017

(54) PIPE CONNECTION STRUCTURE IN ENDOSCOPE AND PRODUCING METHOD THEREOF

(75) Inventor: Yoshinori Maruyama, Saitama (JP)

(73) Assignee: HOYA CORPORATION, Tokyo (JP)

( * ) Notice: Subject to any disclaimer, the term of this patent is extended or adjusted under 35 U.S.C. 154(b) by 1850 days.

This patent is subject to a terminal disclaimer.

(21) Appl. No.: 12/354,910

(22) Filed: Jan. 16, 2009

(65) Prior Publication Data

US 2009/0187076 A1 Jul. 23, 2009

(30) Foreign Application Priority Data

Jan. 18, 2008 (JP) ................................ 2008-008627

(51) Int. Cl.
| | |
|---|---|
| *B23K 26/00* | (2014.01) |
| *A61B 1/04* | (2006.01) |
| *F16L 13/02* | (2006.01) |
| *A61B 1/00* | (2006.01) |
| *B23K 26/28* | (2014.01) |

(Continued)

(52) U.S. Cl.
CPC ............ *A61B 1/0011* (2013.01); *B23K 26/28* (2013.01); *B23K 26/32* (2013.01); *B23K 26/702* (2015.10); *B24B 9/007* (2013.01); *B23K 26/067* (2013.01); *B23K 2201/04* (2013.01);

(Continued)

(58) Field of Classification Search
CPC ............ B23K 2201/04; B23K 2201/06; B23K 2201/10; B23K 26/242; B23K 26/282; F16L 13/02; F16L 13/0209; F16L 13/0218; F16L 13/0227; F16L 13/0236

USPC ........ 600/130; 285/288.1, 288.3, 288.4, 189, 285/192; 219/617, 619, 121.13, 121.45, (Continued)

(56) References Cited

U.S. PATENT DOCUMENTS 1,883,094 A * 10/1932 Taylor ...................... 285/288.1
3,650,322 A * 3/1972 De Munnik ............. F28F 9/26
165/143

(Continued)

FOREIGN PATENT DOCUMENTS

| | | | |
|---|---|---|---|
| JP | 58-55189 | 4/1983 | |
| JP | S59-189092 | * 10/1984 | ............. B23K 26/28 |

(Continued)

OTHER PUBLICATIONS

Japan Office action, dated Nov. 21, 2012 along with an english translation thereof.
English language Abstract of JP 2003-33320, Feb. 4, 2003.

*Primary Examiner* — Ryan Henderson
*Assistant Examiner* — Aaron B Fairchild
(74) *Attorney, Agent, or Firm* — Greenblum & Bernstein, P.L.C.

(57) ABSTRACT

A pipe connection structure for an endoscope is provided with a pipe made of a corrosion-resistant alloy material, and a piping block made of a corrosion-resistant alloy material, the piping block having a pipe insertion hole. An end of the pipe is fitted in the pipe insertion hole and the pipe and the piping block are connected by welding by irradiating a laser beam on the entire circumference of an area where the end of the pipe is fitted in the hole formed on the piping block. An axial length of the pipe inserted in the pipe insertion hole is in a range of 0.5 to 2 times a wall thickness of the pipe.

5 Claims, 3 Drawing Sheets

(51) Int. Cl.
*B24B 9/00* (2006.01)
*B23K 26/32* (2014.01)
*B23K 26/70* (2014.01)
B23K 26/067 (2006.01)
B23K 101/04 (2006.01)
B23K 103/02 (2006.01)
B23K 103/00 (2006.01)

(52) U.S. Cl.
CPC ...... *B23K 2203/02* (2013.01); *B23K 2203/50* (2015.10); *F16L 13/02* (2013.01)

(58) Field of Classification Search
USPC .................. 219/121.6–121.86, 136; 29/428; 228/112.1
See application file for complete search history.

(56) References Cited

U.S. PATENT DOCUMENTS

| | | | |
|---|---|---|---|
| 4,000,392 A | 12/1976 | Banas et al. | |
| 4,533,806 A | 8/1985 | Kawasaki et al. | |
| 4,684,779 A | 8/1987 | Berlinger et al. | |
| 4,723,064 A | 2/1988 | Bothe, II | |
| 5,001,323 A | 3/1991 | Matsutani et al. | |
| 5,172,939 A * | 12/1992 | Hashimoto | 285/24 |
| 5,840,015 A | 11/1998 | Ogino | |
| 5,864,111 A | 1/1999 | Barefoot | |
| 5,887,910 A * | 3/1999 | Usui | 285/288.1 |
| 5,977,513 A | 11/1999 | Findlan | |
| 8,053,702 B2 * | 11/2011 | Maruyama | 219/121.64 |
| 2002/0017515 A1 | 2/2002 | Obata et al. | |
| 2005/0077343 A1 | 4/2005 | Sato et al. | |
| 2005/0137453 A1 | 6/2005 | Ouchi et al. | |
| 2006/0155271 A1 | 7/2006 | Sugita et al. | |
| 2006/0271066 A1 | 11/2006 | Kimura et al. | |
| 2007/0043324 A1 | 2/2007 | Shibata et al. | |
| 2007/0203487 A1 | 8/2007 | Sugita | |
| 2007/0236782 A1 | 10/2007 | Sano | |
| 2007/0282326 A1 | 12/2007 | Sugita | |

FOREIGN PATENT DOCUMENTS

| | | | |
|---|---|---|---|
| JP | 4-25007 | 4/1992 | |
| JP | 4-162973 | 6/1992 | |
| JP | 7-255664 | 10/1995 | |
| JP | 2003-33320 | 2/2003 | |
| JP | 2004-283883 * | 10/2004 | ............ B23K 26/00 |
| JP | 2006-223518 | 8/2006 | |

* cited by examiner

PIPE CONNECTION STRUCTURE IN ENDOSCOPE AND PRODUCING METHOD THEREOF

BACKGROUND OF THE INVENTION

Technical Field

The present invention relates to a pipe connection structure of an endoscope and a producing method thereof.

Related Art

Generally, pipe connection structures in endoscopes configured such that one end of a pipe made of a corrosion-resistant alloy material is fitted in a pipe insertion hole which is formed in a piping block made of a corrosion-resistant alloy material and fixed. Then, the pipe and the piping block are welded by irradiating a laser beam on the entire circumference of the exterior edge of their inter-fit area. An example of such a technique is disclosed, in Japanese Published Examined Application No. HEI 4-25007.

In a pipe and a piping block, their respective metals are melted at the laser beam-irradiated portion and a portion in the close vicinity thereof, whereby they are connected integrally. In the inter-fit area of the pipe and the piping block, an opposite side of the melted portion may not be welded and a gap may be left between the portions where the pipe and the piping block.

SUMMARY OF THE INVENTION

At the pipe connection structure of an endoscope, the pipe passage communicates with the inside of human body during endoscopic investigation. Therefore, if there is a gap in the portion behind the inter-fit area between the pipe and the piping block, filthy liquid may be collected thereat, which may become a source of infection. However, if the inter-fit length is too short, sufficient connection strength cannot be achieved. Further, a leakage of liquid from the inter-fit area is not allowed.

Aspects of the present invention provide a pipe connection structure of an endoscope and a producing method thereof in which a pipe and a piping block can be connected and fixed with sufficient strength and no leakage by laser welding without causing pooling of filthy liquid.

Means for Solving the Problem

According to aspects of the invention, there is provided a pipe connection structure for an endoscope, which is provided with a pipe made of a corrosion-resistant alloy material, and a piping block made of a corrosion-resistant alloy material, the piping block having a pipe insertion hole. An end of the pipe is fitted in the pipe insertion hole and the pipe and the piping block are connected by welding by irradiating a laser beam on the entire circumference of an area where the end of the pipe is fitted in the hole formed on the piping block. An axial length of the pipe inserted in the pipe insertion hole is in a range of 0.5 to 2 times a wall thickness of the pipe.

According to aspects of the invention, there is provided a method of producing a pipe connection structure for an endoscope, comprising a step of preparing a pipe made of a corrosion-resistant alloy material, a step of preparing a piping block made of a corrosion-resistant alloy material, the piping block having a pipe insertion hole, a step of fitting an end of the pipe in the pipe insertion hole, and a step of connecting the pipe and the piping block by welding by irradiating a laser beam on the entire circumference of an area where the end of the pipe is fitted in the hole formed on the piping block, an axial length of the pipe inserted in the pipe insertion hole is in a range of 0.5 to 2 times a wall thickness of the pipe.

According to aspects of the present invention, the pipe and the piping block can be securely connected with sufficient strength by laser welding without causing collection of filthy liquid and leak of liquid.

BRIEF DESCRIPTION OF THE ACCOMPANYING DRAWINGS

DETAILED DESCRIPTION OF THE EMBODIMENT

Hereinafter, referring to accompanying drawings, embodiments of the present invention will be described.

Figure 3:
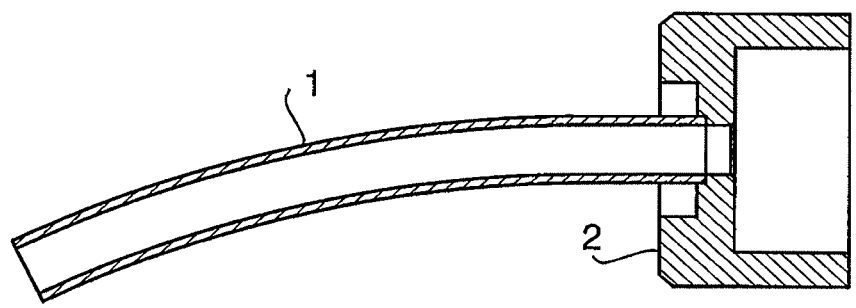
FIG. 3 is a cross sectional side view of the pipe connection structure of the endoscope according to the embodiment of the invention.

FIG. 3 shows a pipe connection structure which forms a suction pipe-line and the like in an endoscope. An example of an endoscope having a pipe connection structure, to which the embodiments of the invention are applicable, is U.S. Pat. No. 5,840,015, teachings of which are incorporated herein by reference. In the example shown in FIG. 3, one end of a pipe 1 for allowing fluid to pass through is connected with a piping block 2 and fixed thereto. The piping block 2 is formed in the shape of a hollow cylinder with one end side is closed. Each of the pipe 1 and the piping block 2 is a hollow cylindrical member made of a corrosion-resistant alloy material such as stainless steel (e.g., SUS 304).

Figure 1:
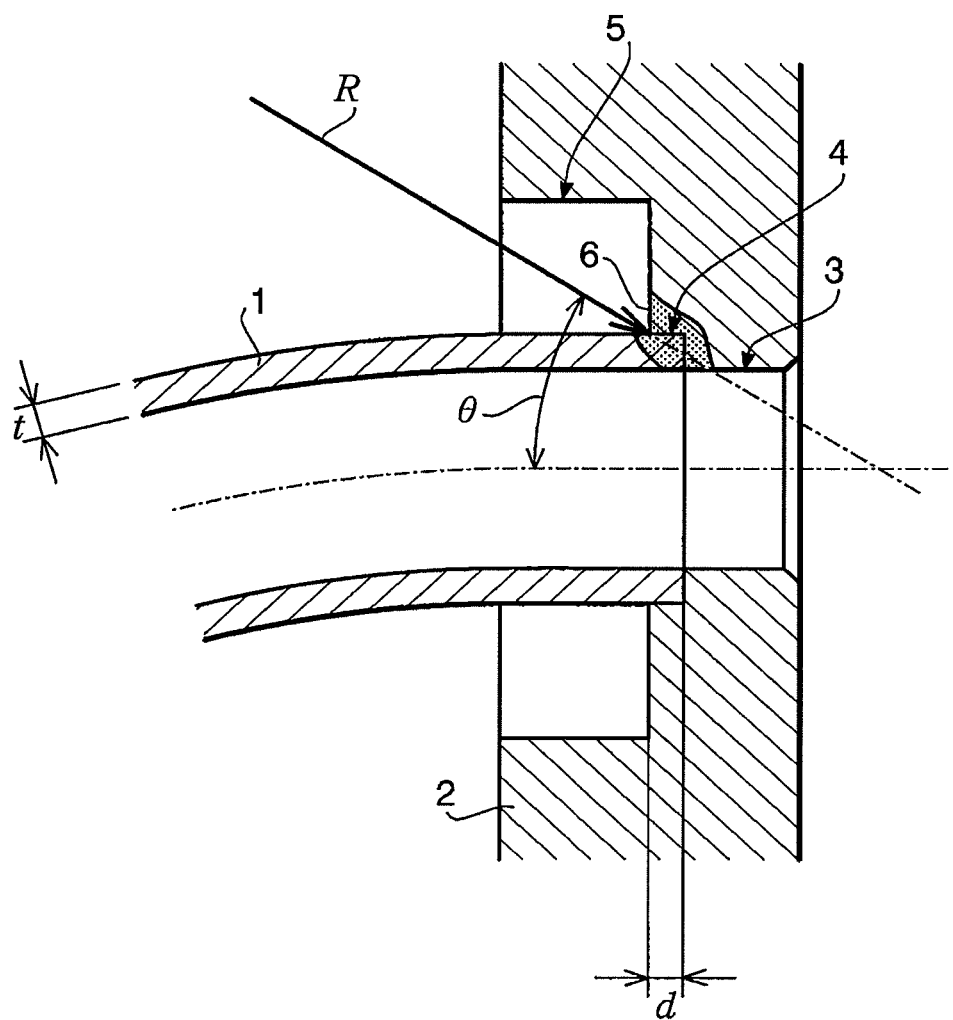
FIG. 1 is an enlarged cross sectional side view of a pipe connection structure of an endoscope according to an embodiment of the invention.
Figure 2:
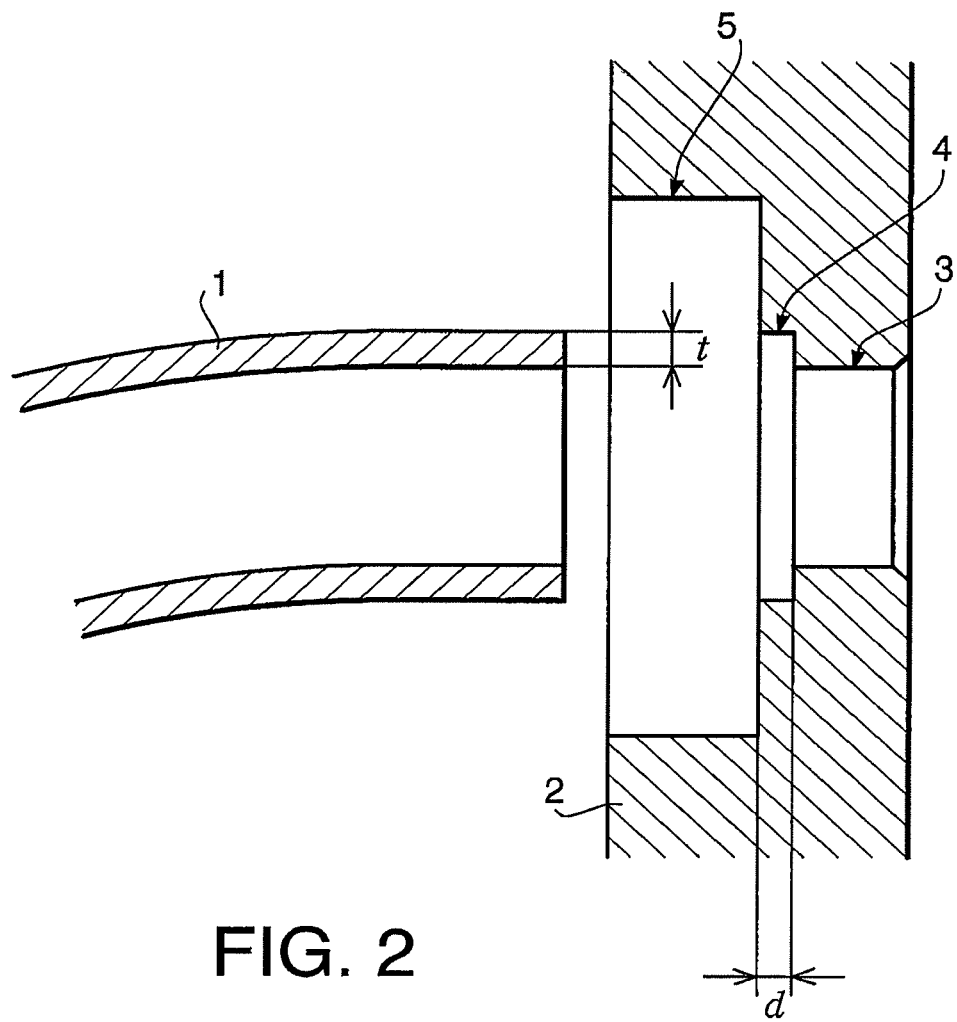
FIG. 2 is an enlarged cross sectional side view of the pipe connection structure of the endoscope in a pre-connection state, according to the embodiment of the invention.

FIG. 1 shows an enlarged view of the area where the pipe 1 and the piping block 2 are connected, and FIG. 2 shows the pipe 1 and the piping block 2 before they are connected. In the piping block 2, a communicating hole 3 is formed. The communication hole 3 has substantially the same inner diameter size as that of the pipe 1.

A pipe insertion hole 4 having an inner diameter which is sized to fit with the end of the pipe 1 and is formed to have a diameter slightly larger than the inner diameter of the communicating hole 3. The pipe insertion hole 4 is formed to have a shoulder to which the end surface of the pipe 1 is contacted. The piping block 2 is further provided with a clearance hole 5 which is formed to be a large diameter on the surface from which the pipe 1 is inserted. The communicating hole 3, the pipe insertion hole 4 and the clearance hole 5 are formed coaxially, and are arranged along the central axis of the coaxially provided holes. The pipe insertion hole 4 is formed such that the pipe 1 tightly fits in the pipe insertion hole 4 without loosening (e.g., an outer diameter of the pipe 1 plus 0.05 mm or less).

The depth d of the pipe insertion hole 4 (i.e., an inter-fit length along the axis of the pipe 1 with respect to the insert hole 4) is substantially equal to the wall thickness t of the pipe 1. That is, d≈t, in FIG. 1.

As shown in FIG. 1, a laser beam R is emitted from outside toward the entire circumference of the exterior edge of the inter-fit area when one end of the pipe 1 is fitted in the pipe insertion hole 4. With this process, the pipe 1 and the piping block 2 are securely connected by welding (seam welding). In FIG. 1, the portion indicated by a numeral 6 is the welded area where the pipe 1 and piping block 2 are fused and integrally connected.

The laser beam R is emitted from outside toward the entire circumference of the exterior edge of the inter-fit area of the pipe 1 and the pipe insertion hole 4 at an angle of 5 to 60 degrees (i.e., 5°≤θ≤60°) with respect to the axis of the end side of the pipe 1.

When the irradiation angle θ is smaller than 5 degrees or larger than 60 degrees, it becomes difficult to accurately irradiate with the laser beam R on the exterior edge of the inter-fit area of the pipe 1 and the pipe insertion hole 4. Incidentally, a YAG laser is used as the laser beam R, for example.

When the pipe 1 and the piping block 2 are welded according to the above manner, since the inter-fit length d of the pipe 1 with respect to the insert hole 4 is substantially the same as the wall thickness t of the pipe 1, the inter-fit area is included in the welded area 6, and no gap is left in the inter-fit area.

Therefore, the pipe 1 and the piping block 2 can be connected with sufficient strength without causing collection of filthy liquid and leakage thereof. Moreover, the welding can be completed in a very short time, for example, approximately in ten seconds.

It should be noted that, when the inter-fit length d of the pipe 1 is approximately no more than 2 times the wall thickness t of the pipe 1, the inter-fit area is wholly included in the welded area 6, and no gap is left. When the inter-fit length d is approximately at least 0.5 times the wall thickness t, sufficient welding strength can be achieved. Therefore, the inter-fit length d along the axis of the pipe 1 with respect to the insert hole 4 may be in the range of 0.5 to 2 times the wall thickness t of the pipe 1.

Figure 4:
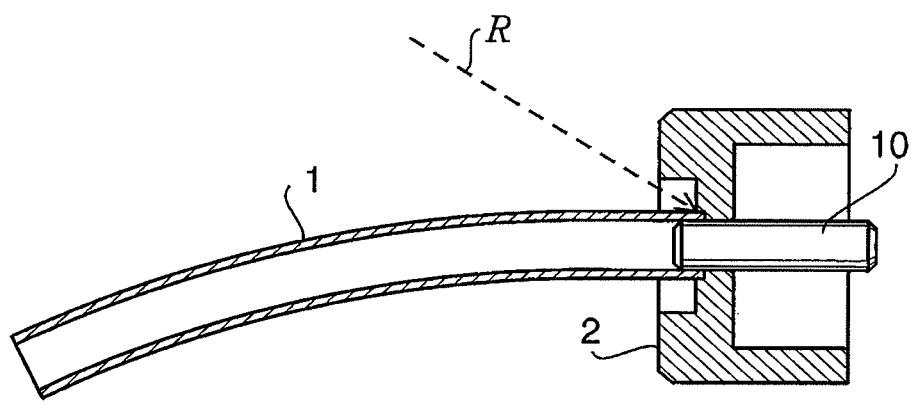
FIG. 4 is a cross sectional side view of the pipe connection structure with a rod-shaped member being inserted for the laser irradiation, according to an embodiment of the invention.

FIG. 4 shows a condition where a solid or a hollow rod-shaped (i.e., cylindrical) member 10 made of a material such as copper, which is infusible by the laser beam R of a YAG laser is fitted in the pipe 1 and the piping block 2 during the irradiation with laser beam R for connecting the pipe 1 and the piping block 2.

The rod-shaped member 10 is inserted from the outside and is fitted in the pipe 1 at a position corresponding to the area irradiated with the laser beam R. With the rod-shaped member 10, irradiation of the laser beam R to portions which should not be or are unnecessary to be irradiated can be prevented.

Further, each internal wall surface of the pipe 1 and the piping block 2 can be prevented from being finished as a rough uneven state. Incidentally, the rod-shaped member 10 may be made of gold or silver, however, the costs will be increased.

Figure 5:
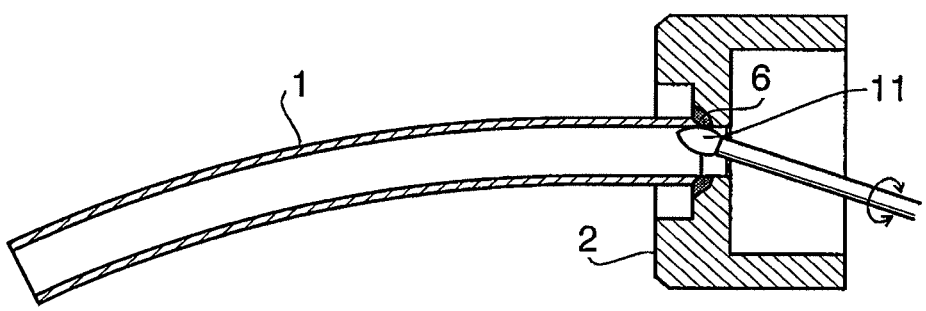
FIG. 5 is a cross sectional side view of a pipe connection structure when the inner surface of the pipe connection structure is finished, according to the embodiment of the invention.

Optionally, when the laser beam R irradiation process has been finished, as shown in FIG. 5, the internal wall surface of the welded area 6 of the pipe 1 and the piping block 2 which have been roughened by the laser beam R irradiation may be finished to be a smooth surface with polishing using a micro grindstone 11 and the like.

According to the above-described embodiment, the pipe 1 is fitted in the insert hole 4 formed on the piping block 2 for temporarily fixing the connection therebetween. At this stage, the end of the pipe 1 is abutted against the bottom surface of the insert hole 4. Then, by appropriately adjusting the welding depth of the laser beam R, the fitted portions of the pipe 1 and piping block 2, and the bottom of the insert hole 4 against which the end of the pipe 1 is abut are welded. Since the connected portions are completely molten and then connected integrally, no interspace is formed therebetween.

The present disclosure relates to the subject matters contained in Japanese Patent Applications No. 2008-008627, filed on Jan. 18, 2008, and No. 2008-239029, filed on Sep. 18, 2008, which are expressly incorporated herein by reference in their entireties.

What is claimed is:

1. An endoscope having a pipe connection structure, comprising:
  a pipe of a corrosion-resistant alloy material; and
  a piping block of a corrosion-resistant alloy material, the piping block having a pipe insertion hole and a clearance hole, the clearance hole configured such that, when the pipe is inserted in the insertion hole, a gap is provided between the pipe and a surface of the clearance hole facing the pipe, a diameter of the clearance hole being larger than a diameter of the pipe insertion hole, the clearance hole being coaxial with the pipe insertion hole, one end of the pipe being configured to connect to the piping block, an other end of the pipe being configured to be connected to an insertion portion of the endoscope that is insertable into a body,
  wherein an end of the pipe is in the pipe insertion hole, and between the pipe and the piping block laser beam irradiated weld material extends about an entire circumference of an inter-fit area between the end of the pipe and the pipe insertion hole of the piping block, the inter-fit area being the entire immediately pre weld contact area between the pipe and the piping block, the weld material penetrating into the entire inter-fit area, an axial length of the pipe inserted in the pipe insertion hole is in a range of 0.5 to 2 times a wall thickness of the pipe.

2. The endoscope having a pipe connection structure according to claim 1, wherein the axial length of the pipe inserted in the pipe insertion hole is substantially the same as the wall thickness of the pipe.

3. The endoscope having a pipe connection structure according to claim 1, wherein the piping block is provided with a communication hole, the communication hole communicating with the inside of the pipe, the pipe insertion hole and the communication hole being arranged next to each other, the pipe insertion hole having a larger diameter than the communication hole so that a step is formed between the pipe insertion hole and the communication hole, an end side surface of the pipe contacting the step between the pipe insertion hole and the communication hole.

4. The endoscope having a pipe connection structure according to claim 1, the clearance hole, the pipe insertion hole, and a communication hole that communicates with the inside of the pipe, which is positioned adjacent to the pipe insertion hole and has a diameter smaller than a diameter of the pipe insertion hole, are coaxially arranged.

5. The endoscope having a pipe connection structure according to claim 1, the clearance hole providing access to the pipe insertion hole.

* * * * *